United States Patent

Schumacher

(10) Patent No.: US 6,586,739 B2
(45) Date of Patent: Jul. 1, 2003

(54) DEVICE FOR DETECTING CHARACTERISTICS OF A MOVING PAPER WEB

(75) Inventor: Ursula Schumacher, Jülich (DE)

(73) Assignee: Metso Automation Oy, Helsinski (FI)

( * ) Notice: Subject to any disclaimer, the term of this patent is extended or adjusted under 35 U.S.C. 154(b) by 0 days.

(21) Appl. No.: 10/167,105

(22) Filed: Jun. 11, 2002

(65) Prior Publication Data
US 2002/0180976 A1 Dec. 5, 2002

Related U.S. Application Data

(63) Continuation of application No. PCT/DE00/04085, filed on Nov. 18, 2000.

(30) Foreign Application Priority Data

Nov. 18, 2000 (DE) .......................................... 199 59 759

(51) Int. Cl.$^7$ .............................................. G01N 21/89
(52) U.S. Cl. ................................ 250/341.1; 250/359.1; 356/429
(58) Field of Search .......................... 250/341.1, 341.8, 250/359.1, 548, 559.01, 559.05, 559.06; 356/637, 639, 429, 430, 431

(56) References Cited

U.S. PATENT DOCUMENTS

| 3,859,538 A | | 1/1975 | Mannonen |
| 4,004,152 A | | 1/1977 | Obser et al. |
| 4,204,115 A | * | 5/1980 | Boldridge, Jr. ......... 250/227.11 |
| 4,226,538 A | * | 10/1980 | Van Beeck ................. 356/430 |
| 4,377,746 A | | 3/1983 | Kopineck et al. |
| 4,726,648 A | | 2/1988 | Haberland et al. |
| 4,877,326 A | | 10/1989 | Chadwick et al. |
| 5,064,280 A | * | 11/1991 | Ringens et al. ............. 356/28.5 |
| 5,086,220 A | * | 2/1992 | Berthold et al. ......... 250/227.2 |
| 5,308,964 A | * | 5/1994 | Kwon .................... 235/472.03 |
| 5,323,000 A | * | 6/1994 | Juffinger et al. ........ 250/227.13 |
| 5,347,135 A | * | 9/1994 | Harris et al. ................. 250/548 |
| 5,745,176 A | | 4/1998 | Lebens |
| 5,747,795 A | | 5/1998 | Monney |
| 5,778,124 A | * | 7/1998 | Nedstedt ...................... 385/79 |
| 5,943,127 A | | 8/1999 | Feldman et al. |

FOREIGN PATENT DOCUMENTS

| DE | 19506675 A1 | * | 8/1996 | ............ G02B/6/32 |
| DE | 197 09 963 A1 | | 3/1997 | |
| EP | 0 519 219 A2 | | 12/1992 | |
| EP | 742171 A2 | * | 11/1996 | ............ B65H/43/08 |
| EP | 759568 A1 | * | 2/1997 | ............ G02B/6/32 |
| EP | 0 973 040 A2 | | 1/2000 | |
| GB | 1103491 | | 2/1968 | |
| WO | WO 91/10474 | | 7/1994 | |

* cited by examiner

Primary Examiner—Albert Gagliardi
(74) Attorney, Agent, or Firm—Alston & Bird LLP

(57) ABSTRACT

The invention relates to a device for detecting properties of a moving web of paper, more specifically for production control in the paper making process, with an infrared lighting device suited for illuminating the web of paper with infrared light and provided with a light exit portion, with a detector device for detecting infrared light reflected or transmitted by the web of paper which is provided with a light input portion and with a housing a) which is arranged in immediate proximity to the paper web, b) which is provided with a front face facing the web of paper and c) which accommodates the light exit portion and/or the light input portion provided with optical fibers. A plurality of n spherical lenses is arranged in a sealed manner in the front face, said spherical lenses being each optically coupled to an allocated optical fiber within the housing, said spherical lenses constituting, together with the corresponding optical fibers, the light exit portion and/or the light input portion.

6 Claims, 3 Drawing Sheets

Figure 1:
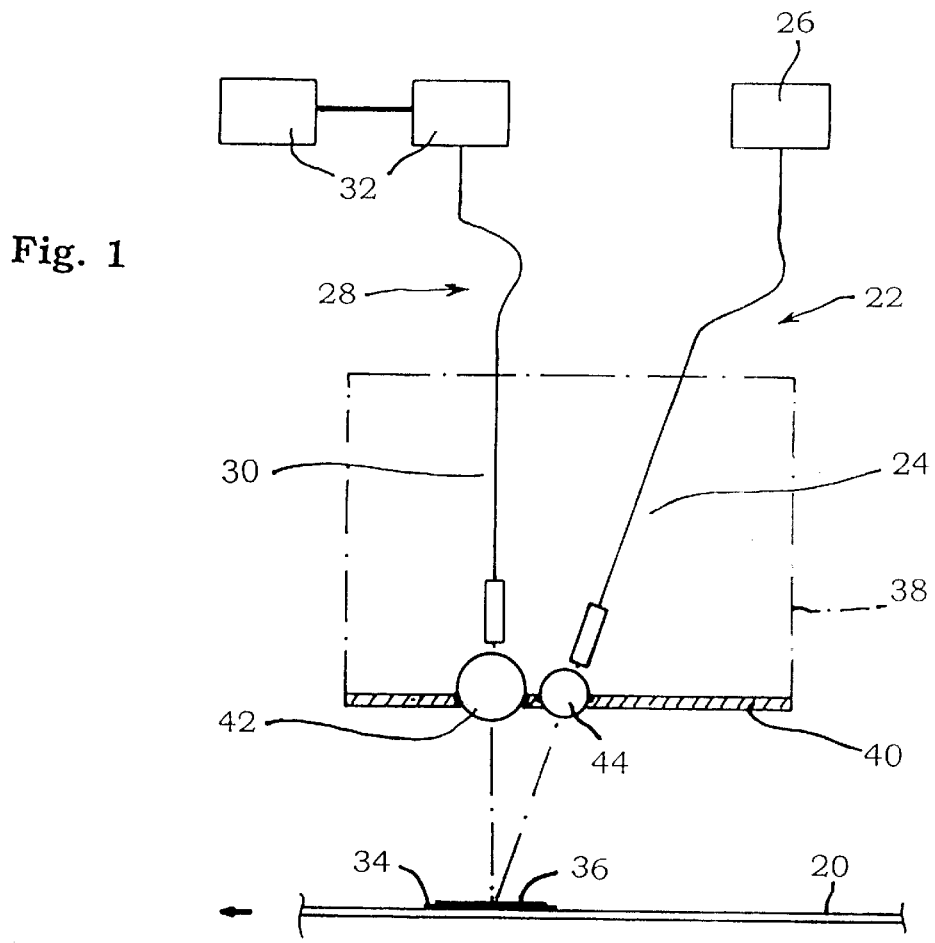

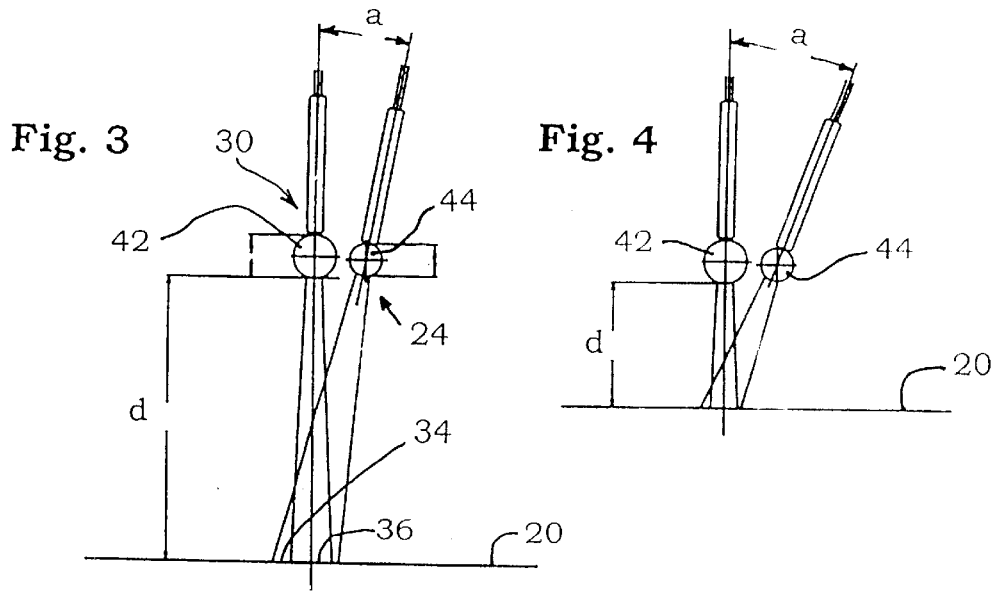
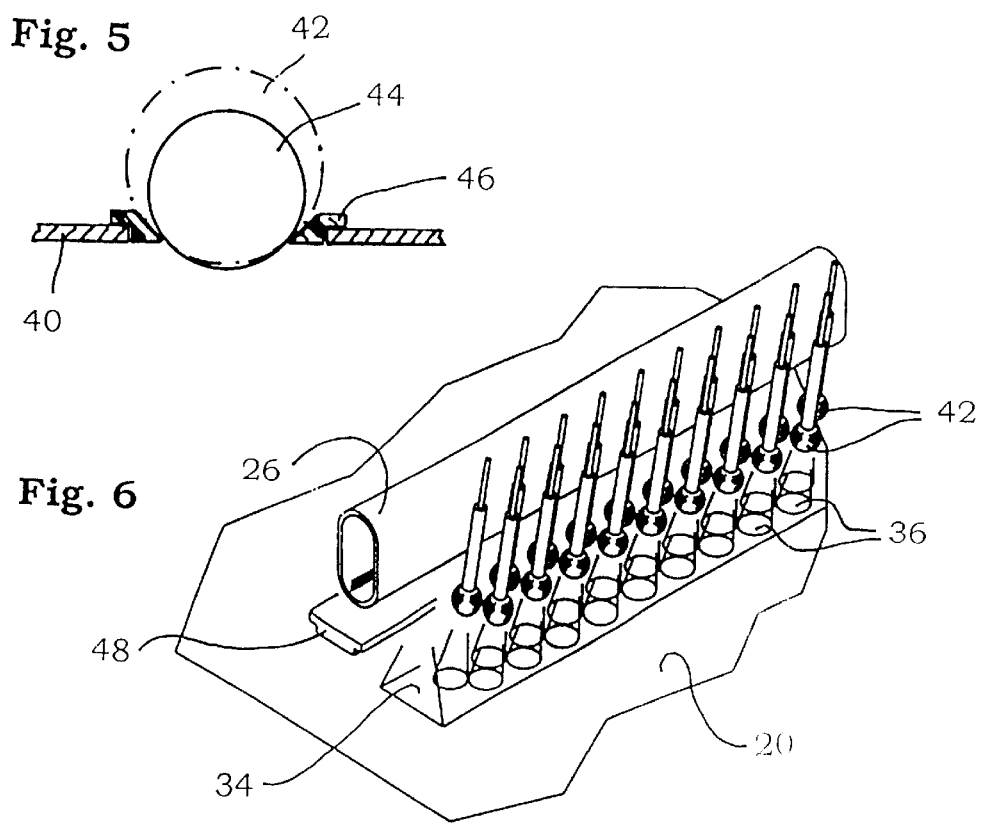

DEVICE FOR DETECTING CHARACTERISTICS OF A MOVING PAPER WEB

CROSS-REFERENCE TO RELATED APPLICATIONS

This application is a continuation of International Patent Application PCT/DE00/04085 filed Nov. 18, 2000, which is incorporated herein by reference.

FIELD OF THE INVENTION

The invention relates to a device for detecting properties of a moving web of paper, more specifically for production control in the paper making process, the device having an infrared lighting device comprising an infrared light source and a light exit portion through which light emitted by the light source exits onto the paper web, having a detector device for detecting infrared light reflected or transmitted by the web of paper which is provided with a light input portion for guiding the reflected or transmitted light to a detector of the detector device, and having a housing a) which is arranged in immediate proximity to the paper web, b) which is provided with a front face facing the web of paper and c) which accommodates the light exit portion and/or the light input portion provided with optical fibers.

BACKGROUND OF THE INVENTION

A device as described above is disclosed in WO 98/40727. In this known device, the web of paper is illuminated by an appropriate source of infrared light. The light input portion is located within the housing, which is substantially configured as a holding member. The light input portion is formed by a plurality of optical waveguides that are arranged side by side in the form of optical fibers of typically between 50 and 600 micrometers thick. The ends of the fibers are polished and oriented to face the web of paper, and are fastened to the housing and project therefrom toward the web of paper.

In principle, this arrangement has proved to be successful. The optical conditions however are not clear, which is disadvantageous. More specifically, the size of the measuring dot on the web of paper is difficult to control and, furthermore, does not apply for many measurement tasks. Furthermore, considerable amounts of dirt, dust and the like are produced in the paper making process. Cleaning the light input portion, more specifically the input ends of the optical fibers, involves difficulties.

Preferably, however, the advantages of the prior art device are to be maintained. The prior art device allows for a high number of measuring dots arranged side by side on the web of paper. Unlike cradles traveling back and forth on crossbars, the device has the advantage that light detection is carried out in a stationary condition relative to the crossbar. The mechanical expenditure needed for performing a reciprocating motion is not required. Moreover, the untested regions of the paper web are smaller than with a cradle traveling back and forth and carrying an optical detector.

SUMMARY OF THE INVENTION

In view of the drawbacks of the device of the type mentioned above, the object of the invention is to allow for a better optical allocation of the light exit portion and/or of the light input portion to the actual measuring dots and to concurrently improve the device in such a manner that it can be readily cleaned when dirty.

The solution to this object is to arrange a plurality of n spherical lenses in a sealed manner in the front face of the device housing, the spherical lenses being each optically coupled to an allocated optical fiber within the housing, the spherical lenses constituting, together with the corresponding optical fibers, the light exit portion and/or the light input portion of the device.

Accordingly, the invention provides the housing with exit windows. These exit windows are configured as spherical lenses, i.e., they also have optical properties. These properties permit to selectively alter the size of the image dot on the web of paper; spherical lenses of various diameters can be used or other optical provisions can be made for this purpose. The spherical lenses are well suited as exit windows; with simple means they can be arranged in a sealed manner in the front face, which is in most cases configured as a front plate. As they are spherical, they need not be oriented in any particular manner and resist high changes in temperature. Similarly, sealing is substantially carried out on a spherical annular region of the spherical lens. On thermal expansion of the materials of the front face and of the spherical lens, the spherical lens can move across the front face without being clamped. Accordingly, it is particularly advantageous to have the spherical lens sealed at some distance from its equator so that the major part of the spherical lenses is located within the housing and only a small part of the sphere protrudes from the front face of the housing toward the web of paper.

The aperture of the optical fibers is corrected or the light is collimated respectively by means of the spherical lenses. The size of the measuring dot on the web of paper can thus be varied; the diameter for example can be varied between 5 mm and 10 mm. In this way, paper can be measured with a sufficient cross sectional resolution of the profile measurement. Depending on the distance from the web of paper, which typically amounts to between 20 and 50 mm, on the size of the measuring dot and on the cross sectional resolution, spheres made of sapphire or of other glasses, which are transmissive to spectroscopy and have a diameter typically ranging from 2 to 10 mm, are used. They are simpler to manufacture than the customary lens-shaped convergent lenses and can be more readily fastened and sealed than the latter.

By virtue of the spherical lenses, the optical images on the paper web can be predetermined and controlled with much more precision. According to the invention in a first embodiment, all of the n spherical lenses are used for the light exit portion; in a second embodiment all of the lenses are used for the light input portion. In a third embodiment a first half n2 is used for the light input portion and the second half n2 for the light exit portion. More particularly, the first half n2 of spherical lenses is connected to optical fibers that lead to a source of infrared light of the infrared lighting device. A second half n2 is connected to respective optical fibers leading to a detecting part, more specifically a polychromator, of the detector device. The optical arrangements are selected such that, with the spherical lenses of the first half, substantially circular illuminated dots are obtained on the web of paper and that, with the spherical lenses of the second half, receiving dots (measuring dots) are obtained that are substantially circular as well, the receiving dots being smaller than the illuminated dots, though. Furthermore, the receiving dots are located within the illuminated dots. It is thus made certain that an optical signal is only acquired from the illuminated regions.

Within the housing, the spherical lenses are optically coupled to optical fibers. The housing is preferably sealed. The coupling region is protected as a result thereof.

Coupling two optical fibers by means of a spherical lens is known. For example, International Wire & Cable Symposium Proc. 1981, p. 341 describes coupling of two optical waveguides by means of spheres. The use of spherical lenses as an exit window and as a front end of a light exit portion or of a light input portion however is not known.

In a preferred embodiment, the spherical lenses are replaceably arranged in the front face so that spherical lenses of different diameters can be mounted into the front face. Different images can thus be obtained depending on the purpose of the measurement. The spherical lenses are preferably sapphire spheres, which are available at low cost on the market and have a high degree of hardness. Therefore, they can be readily cleaned without having to fear scratches.

Preferably, the plurality of n spherical lenses is accommodated in regular arrangement in the front face. The regular arrangement permits to assign with precision the illuminated dot formed by the light exit portion on the paper web and the corresponding receiving dot detected by the corresponding light input portion.

In another preferred embodiment, the plurality of n spherical lenses is connected to optical fibers leading to a detecting part, more specifically a polychromator, of the detector device and an infrared light source in the form of an elongated, linear radiating element is provided in the housing, the radiating element being allocated an exit window in the housing, more specifically an elongated cylindrical lens in the form of a rod which substantially is of the same length as the radiating element and is mounted into the front face so as to be sealed. The optical arrangements are thereby such that an elongated, narrow illuminated dot is projected on the web of paper while the n spherical lenses provide substantially circular receiving dots, the receiving dots being located side by side inside the elongated illuminated dot. Again, the optical conditions are predetermined in such a manner that only such optical signals are received and interpreted later on that originate from illuminated regions of the web of paper.

Although the device in accordance with the invention is in principle suited for light of any wavelength, it is preferably designed for the near infrared, by which the wavelength range above the visible range (above approximately 800 nm), more specifically 1.5 to 2.5 $\mu$m, is meant.

In a particularly preferred embodiment there is provided a cleaning device which is designed to clean those portions of the spherical lenses and their surroundings that are accessible from the outside on the front face and that are oriented toward the web of paper. It is thus made certain that dirt, which cannot be excluded, can be removed and that the optical conditions can repeatedly be restored to their initial condition even when the paper making process is continuous and lasts for many months.

Preferably, the housing is configured in a substantially elongated shape, more specifically to give it a length of at least one meter. The usual widths of paper webs require several such housings that are arranged side by side in a staggered pattern on a stationary crossbar. To permit the exchange of individual housings during the paper making process, at least some of the housings are connected to the crossbar by way of a longitudinal guide along which they are slidable relative to the crossbar. Individual housings can thus be removed from the crossbar without disturbing the paper making process.

BRIEF DESCRIPTION OF THE SEVERAL VIEWS OF THE DRAWING(S)

Figure 2:
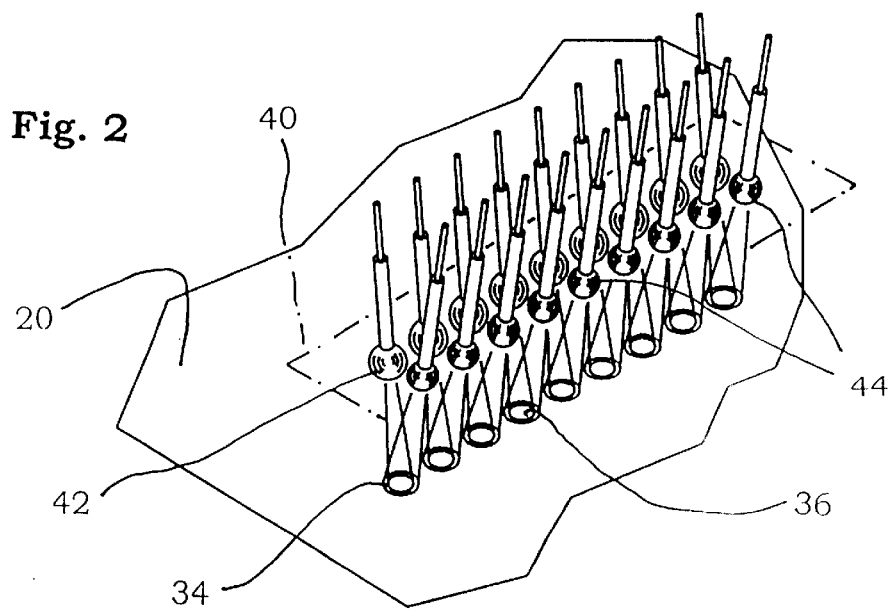
Figure 7:
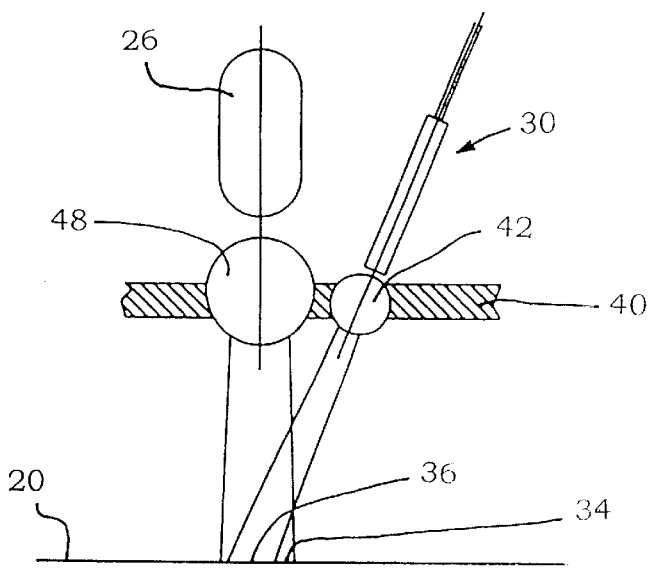
Figure 8:
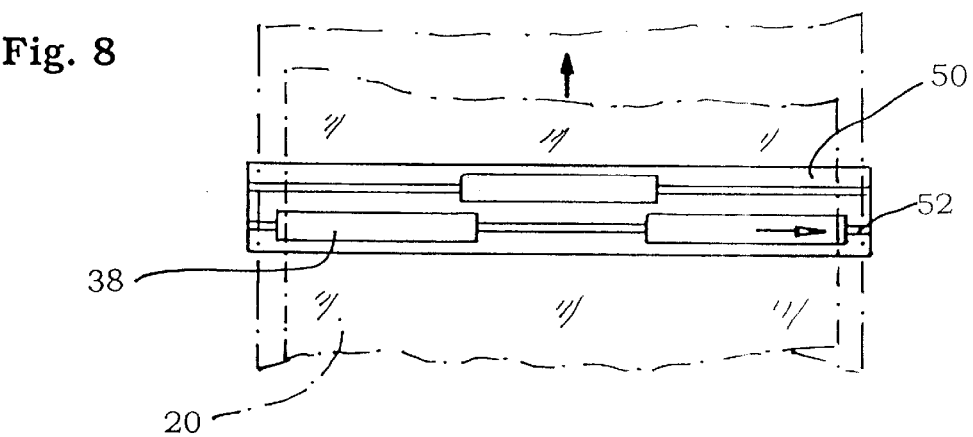
Figure 9:
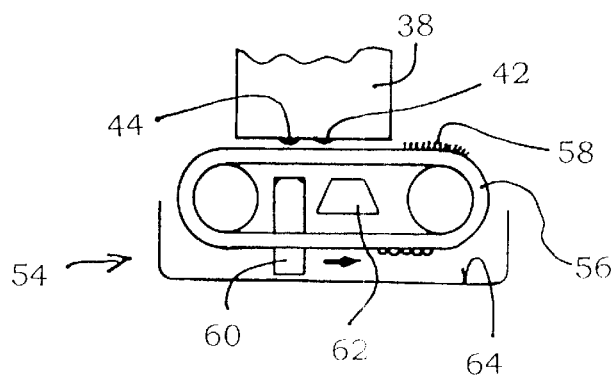

Having thus described the invention in general terms, reference will now be made to the accompanying drawings, which are not necessarily drawn to scale, and wherein:

FIG. 1 is a diagrammatic side view of a device for detecting properties of a moving web of paper in accordance with the invention, FIG. 2 is a perspective view of a web of paper onto which are directed the light exit portions and the light input portions of the device according to FIG. 1, FIG. 3 is a view similar to FIG. 1, FIG. 4 is a view similar to FIG. 3 explaining, in connection with FIG. 3, the setting of an illuminated dot, FIG. 5 is a sectional view through a front face similar to FIG. 1 showing the arrangement and the sealing of spherical lenses of different diameters, FIG. 6 is a view similar to FIG. 2 but with an infrared lighting device in the form of an elongated rod, FIG. 7 is a view similar to FIG. 3, for the arrangement according to FIG. 6, FIG. 8 is a bottom view through a conveyed web of paper shown in dash-dot line and arranged on a crossbar with three housings, and FIG. 9 is a diagrammatic side view of a cleaning device located underneath the housing.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

FIG. 1 illustrates a device for detecting properties of a moving web of paper 20, the motion being indicated by an arrow. It has an infrared lighting device 22 which is provided, in the exemplary embodiment of concern, with a light exit portion 24 and with a source of infrared light 26. It also has a detector device 28 provided with a light input portion 30 and with an evaluation unit 32 arranged downstream thereof and including for example a polychromator with an infrared photoconductor array and an electronic equipment connected downstream thereof.

The web of paper 20 is illuminated by regions by means of the infrared lighting device 22. In particular, a plurality of illuminated dots 34 are produced on the web of paper 20, FIG. 1 showing only one such dot 34. Each illuminated dot 34 is allocated one single light input portion 30 that acquires information data from one measuring dot or receiving dot 36 located within the illuminated dot 34. Usually, these dots 34, 36 are circular as shown in FIG. 2.

The individual light exit portions 24 and the individual light input portions 30 are arranged in a housing 38 which is sealed from the outside. It has one front face 40 that faces the web of paper 20 and is configured as a front plate here, but it can be other shapes. It is arranged in immediate proximity to the web of paper 20. As can be seen from FIG. 1, both the light exit portion 24 and the light input portion 30 have optical fibers or optical waveguides for making the optical connections.

As more particularly shown in FIGS. 1 and 5, a plurality of spherical lenses 42, 44 are arranged in the front face in a sealed manner. The number of spherical lenses 42, 44 amounts to n. Preferably, larger spherical lenses 42 are provided, which are assigned to the light input portion 30, and smaller spherical lenses 44 are provided, which are assigned to the light exit portion 24. Smaller spherical lenses have a stronger curvature and, consequently, a greater focusing force. In addition, the images can be changed by the spherical lenses by varying the distance of the exit ends of the optical fibers from the respective ones of the spherical lenses 42, 44.

FIG. 2 shows a total of 18 spherical lenses 42, 44, namely nine larger spherical lenses 42 which are allocated respective optical fibers of the detector device 28 and nine smaller spherical lenses 44 which are allocated respective optical fibers of the light exit portion 24. They are arranged in a front face 40 which is shown in a dash-dot line. The arrangement is regular. The individual illuminated dots 34, which are circular, are located so as to be concentric with smaller measuring dots 36 on the web of paper 20.

It can be seen from the FIGS. 3 and 4 that the dots 34, 36 can be adjusted relative to each other by merely adjusting the angle of an optical fiber, in this case the optical fiber of the light exit portion 24. By virtue of the spherical lenses 42, 44, no further adjustments need be carried out. FIG. 4 shows that, in increasing the angle a, the spacing between the spherical lenses 42, 44 and the paper web can be adjusted from a greater spacing (FIG. 3) to a smaller spacing (FIG. 4). As a result thereof, the housing 38 can be adjusted to various distances from the web of paper 20.

The spherical lenses project from the lower side of the front face 40 downward, toward the web of paper 20. They are arranged in the front plate in a sealed manner, as shown in FIG. 5. For this purpose, the front plate 40 is provided with a bore that is limited by an O-ring 46. Spheres of different diameters can be placed thereupon, as shown in FIG. 5. Thus, large and small spherical lenses 42, 44 can be exchangeably mounted. The spherical lenses 42, 44 are pressed against the front plate 40 by way of a simple elastic clamping device (not shown) so that they are capable of moving relative to the front plate.

The arrangement according to FIG. 6 can be compared with that of FIG. 2, but now the illumination is performed by an elongated, rod-shaped source of infrared light such as that offered for sale by the firm of Heraeus (Hanau, Germany) for infrared drying of webs of material in the form of an infrared radiating element of the type ZKA. Such radiating elements have a length of up to two meters and have a particularly large proportion of radiation in the range between 1.2 and 3 micrometers. The radiation is homogeneous over the length of the radiating element. In order to prevent the source of infrared light 26 from getting dirty, a window 48 is inserted in the front face 40. It is sealed relative to the front plate 40. This source of infrared light 26 permits to achieve a long, narrow illuminated dot 34 which, in the illustration, is substantially shaped like an elongated rectangle. The measuring dots 36 are arranged within said illuminated dot 34. They are located below the total of eighteen spherical lenses, which are all assigned to the light input portion 30.

FIG. 7 shows an arrangement similar to FIG. 6, but the window 48 is no longer a plane-parallel plate, a quartz plate for example; the window 48 now rather has optical properties, preferably being configured as a convergent lens. A rod lens, such as that offered for sale by Edmund Scientific under the name of Micro-Rod, preferably is utilized. It acts as a spherical lens and collimates the light so that the illuminated dot 34 obtained is elongated and of about 5 to 10 mm wide. Such a rod lens is easier to arrange in a sealed manner in the front plate 40 than a plate, since it can be caused to move across the front plate 40 by relative thermal expansion, just as this is possible with the spherical lenses 42, 44 also. Owing to its shape, which resembles more the shape of a sphere, the rod lens is less prone to break than the plate when subjected to thermal tensions.

Again, and analogous to the case illustrated in the FIGS. 3 and 4, the distance d from the web of paper 20 can be adjusted by changing the angular position of the optical fibers of the light input portion 30.

FIG. 8 is a bottom view through a web of paper 20 shown in a dash-dot line, showing a stationary crossbar 50 that is connected to a part of a paper machine which is also shown in a dash-dot line. Rails 52 are arranged on the bottom side of the crossbar 50. Elongated housings 38 are connected to the rails, light exit portions 24 and light input portions 30 being arranged in the housings in accordance with the FIGS. 2, 6 or 7. The configuration according to FIG. 8 is preferably intended to be used with the rod-shaped infrared light sources 26 according to FIGS. 6 and 7. To span a web of paper 20 of many meters wide, several housings 38 are arranged in a staggered pattern so that the entire width of the paper web 20 can be measured on a continuous basis.

FIG. 9 shows a cleaning device that is shown only in principle. It shows a housing 38 from the bottom of which spherical lenses 42, 44 or a rod lens 48 protrude slightly. The cleaning device 54 has an endless belt 56 that is supported on the right and on the left side thereof by two rolls and which is driven, the drive occurring in the direction of the arrow. Brushes 58 for cleaning the bottom face of the front plate 40, and more specifically those parts of the spherical lenses 42, 44 that are visible from underneath, are for example located on the belt. Drying devices and so on are also provided on the belt 56. For cleaning, a cleansing fluid is sprayed from the bottom onto the front face 40 by means of a spraying device 60, the fluid being sucked off again by a suction device 62. A trough 64 is located underneath the cleaning device 54, so that other parts are not soiled in the process.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A device for detecting properties of a moving web of paper, comprising:

an infrared lighting device for illuminating the web of paper with infrared light, said infrared lighting device having an infrared light source and a light exit portion, a detector device for detecting infrared light reflected or transmitted by the web of paper said detector device having a light input portion, and a housing arranged in immediate proximity to the paper web and having a front face facing the web of paper, wherein at least one of the light exit portion and the light input portion is provided with optical fibers and is accommodated within the housing, wherein a plurality of n spherical lenses are arranged in the front face, said lenses forming exit and/or input windows, each of the spherical lenses is optically coupled within the housing to a respective one of the optical fibers by forming a coupling region therewith, said spherical lenses forming, together with the corresponding optical fibers, the at least one of the light exit portion and the light input portion, the spherical lenses are arranged in a sealed manner in the front face so that the housing is sealed and the coupling regions thus protected, and the spherical lenses are replaceably arranged in the front face so that spherical lenses of different diameters can be mounted into the front face.

2. The device of claim 1, wherein the plurality of n spherical lenses is arranged in a regular arrangement.

3. The device of claim 1, wherein a first group of the n spherical lenses is connected to optical fibers that lead to the infrared light source of the infrared lighting device and a second group of the n spherical lenses is connected to optical fibers leading to a detecting part of the detector device, and wherein the spherical lenses of the first group are arranged so as to produce substantially circular illuminated dots on the web of paper and the spherical lenses of the second group are arranged so as to provide receiving dots that are substantially circular as well, but that are smaller than the illuminated dots and are located within said illuminated dots.

4. The device of claim 1, wherein the n spherical lenses are connected to optical fibers leading to a detecting part of the detector device and wherein the infrared light source comprises an elongated, linear radiating element provided in the housing and an elongated cylindrical lens in the form of a rod which is substantially the same length as the radiating element and is mounted into the front face so as to be sealed, and wherein the radiating element and cylindrical lens are arranged so that an elongated, narrow illuminated dot is projected on the web of paper and the n spherical lenses are arranged so that substantially circular receiving dots are obtained, said receiving dots being located side by side inside the illuminated dot.

5. The device of claim 4, wherein the housing has an elongated shape and is arranged with several other such housings side by side on a crossbar extending transversely to the moving web of paper and wherein the housing is connected to a longitudinal guide and is slidable relative to the crossbar along said longitudinal guide.

6. The device of claim 1, wherein a cleaning device is provided, said cleaning device being adapted to clean, in a cleaning procedure, those parts of the spherical lenses and their surroundings that are accessible from the outside on the front face.

* * * * *

UNITED STATES PATENT AND TRADEMARK OFFICE
CERTIFICATE OF CORRECTION

PATENT NO.   : 6,586,739 B2                                                                     Page 1 of 1
DATED         : July 1, 2003
INVENTOR(S)  : Schumacher It is certified that error appears in the above-identified patent and that said Letters Patent is hereby corrected as shown below:

<u>Title page,</u>
Item [30], Foreign Application Priority Data,
"Nov. 18, 2000" should read -- Dec. 11, 1999 --.

Signed and Sealed this

Fourteenth Day of October, 2003

JAMES E. ROGAN
*Director of the United States Patent and Trademark Office*